United States Patent [19]

Cochrane et al.

[11] 4,225,982
[45] Oct. 7, 1980

[54] MOLDED SYME FOOT WITH ATTACHED STUMP SOCKET

[76] Inventors: Ian W. Cochrane, 87 Wexford St. N., Winnipeg, Manitoba, Canada R3R 0R6; Frederick R. Tucker, deceased, late of Winnipeg, Canada; by Mary Tucker, co-executrix, 138 Buxton Rd., Winnipeg, Manitoba, Canada; by George Ackerman, co-executor, 12 Beaumont Bay, Winnipeg, Manitoba, Canada; by Canada Permanent Trust Co., co-executor, 433 Portage Ave., Winnipeg, Manitoba, Canada. R3B 2C9

[21] Appl. No.: 966,362

[22] Filed: Dec. 4, 1978

[51] Int. Cl.³ .......................... A61F 1/08; A61F 1/02; A61F 1/04
[52] U.S. Cl. ............................................. 3/7; 3/17 R; 3/30
[58] Field of Search ........................................... 3/6–8, 3/30–35, 2, 17–19

[56] References Cited
U.S. PATENT DOCUMENTS

| | | | |
|---|---|---|---|
| 1,323,444 | 12/1919 | Bowler | 3/33 |
| 3,833,941 | 9/1974 | Wagner | 3/7 |
| 3,874,004 | 4/1975 | May | 3/7 X |
| 3,890,650 | 6/1975 | Prahl | 3/7 |
| 4,091,472 | 5/1978 | Daher et al. | 3/7 |

FOREIGN PATENT DOCUMENTS 165914  5/1950  Austria ............................................. 3/6

OTHER PUBLICATIONS

"An Innovation in Symes Prosthetics," by H. W. Marx, Orthotics & Prosthetics, vol. 23, No. 3, Sep. 1969, pp. 131–138.
"Adding Strength to the Syme Prosthesis," by C. H. Dankmeyer, Jr., et al., Orthotics & Prosthetics, vol. 28, No. 3, pp. 3–7, Sep. 1974.

*Primary Examiner*—Ronald L. Frinks
*Attorney, Agent, or Firm*—Stanley G. Ade

[57] ABSTRACT

A flexible precast foot comprises a hollow flexible slipper member which has a rounded heel contour and a keel cavity. The resiliency of the rounded heel is controlled by the type of foam used in order that the compressibility of the heel may be varied during construction. A stump support is custom manufactured from reinforced plastic and the like, from a negative plaster mold and comprises an elongated socket with fenestrations being provided on each side to facilitate the engagement and disengagement of the stump. The negative socket mold is formed by a strip casting plaster technique and the finished positive stump socket is then fitted to the foot and secured to a strip of belting or similar material which extends into the keel cavity. This cavity is filled with "Flexane" rubber or any suitable elastomeric material such as nonfoaming urethane, synthetic rubber which also molds around the distal end of the stump socket. The length of belting together with the elastomeric material filling the keel cavity, controls the toe break of the finished prosthesis.

18 Claims, 15 Drawing Figures

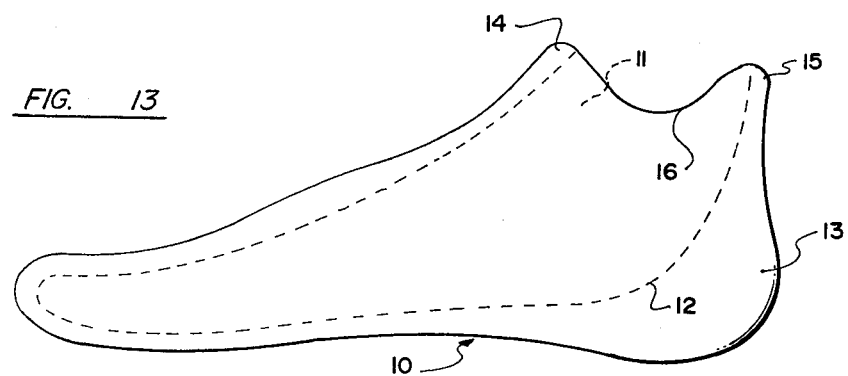
FIG. 13
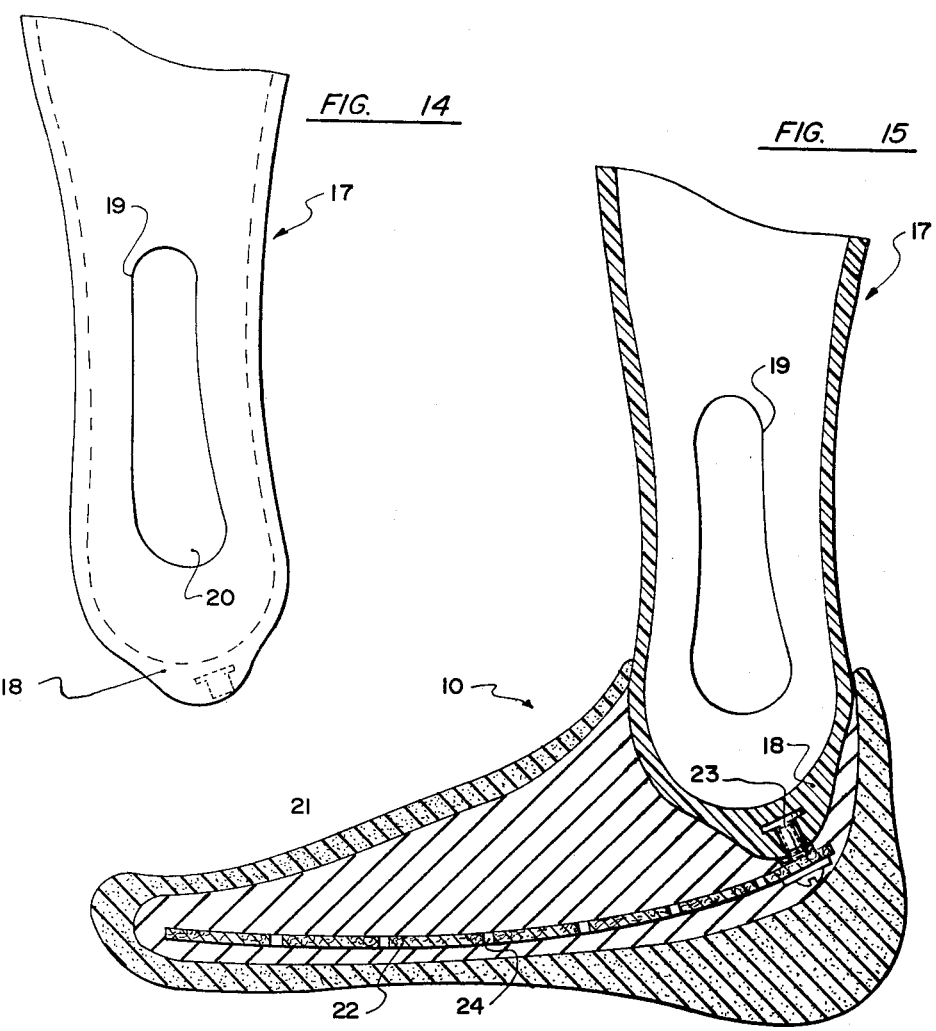
FIG. 14
FIG. 15

MOLDED SYME FOOT WITH ATTACHED STUMP SOCKET

BACKGROUND OF THE INVENTION

This invention relates to new and useful improvements in the construction, fitting and fabrication of a Syme prosthesis.

Attempts have been made in the past to produce a practical flexible Syme socket but this approach to an improved prosthesis has been unsuccessful.

Presently, the conventional Syme prosthesis includes metallic parts, awkward and unsightly construction and lack of flexibility at the toe break together with the lack of adequate compressibility at the heel.

SUMMARY OF THE INVENTION

The present invention overcomes these disadvantages by providing a flexible foot that accepts a semiflexible socket using a mechanical-chemical bonding technique in place of metallic connecting hardware.

The new design provides flexibility at the toe break and adequate compressibility at the heel, two features which are very desirable with the Syme amputation but which are rarely present in the conventional Syme prosthesis.

Furthermore, the cosmesis is greatly improved at the ankle region and because of the elimination of the metallic parts as aforesaid, the wearing effect on clothing is much reduced.

One of the features of the present invention is the provision of a selection of precast feet to which a custom made stump support member is fitted and bonded as will hereinafter be described.

With the foregoing in view, and other advantages as will become apparent to those skilled in the art to which this invention relates as this specification proceeds, the invention is herein described by reference to the accompanying drawings forming a part hereof, which includes a description of the preferred typical embodiment of the principles of the present invention, in which:

DESCRIPTION OF THE DRAWINGS

FIG. 13 is a side elevation of the foot portion per se.

FIG. 14 is a side elevation of the stump support portion per se.

FIG. 15 is a vertical cross sectional view of the assembled prosthesis.

In the drawings like characters of reference indicate corresponding parts in the different figures.

DETAILED DESCRIPTION

Figure 1:
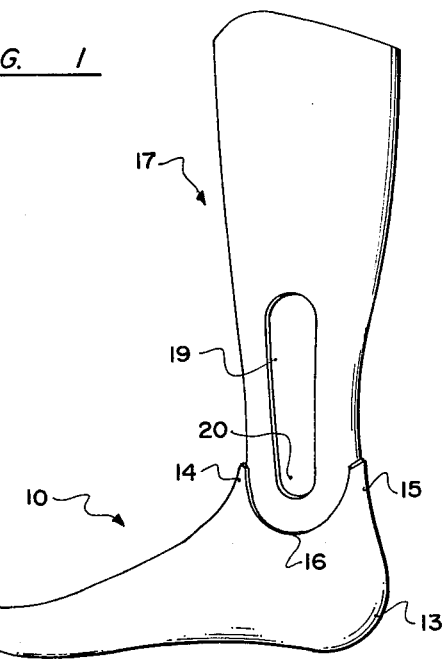
FIG. 1 is a side elevation of the assembled prosthesis.

Proceeding therefore to describe the invention in detail, reference should first be made to FIG. 13 which shows the foot portion per se collectively designated 10. This is a hollow foot produced from a polyurethane flexible foam or the equivalent. Polyurethane foam is not a selfskinning foam but in the present instance, a smooth rubber mold (not illustrated) is used to give a smooth, cosmetically pleasant skin to the finished product.

It is produced with a keel cavity 11, said cavity including the rounded heel contour 12 giving a fairly firm cushioned heel portion 13, the resiliency of which may be controlled due to the type of foam used, in order to vary the compressibility of the heel.

The Syme foot 10 resembles a romeo slipper inasmuch as it is provided with a sole portion, a rounded heel portion, an upper vamp portion and front and rear extensions above the ankle 14 and 15 respectively with the side gores 16 sweeping down on both sides to the level of the ankle joint.

This design facilitates fabrication of the total prosthesis and the attachment of the socket to the foot as will hereinafter be described.

The stump support portion collectively designated 17 is manufactured from reinforced plastic which may utilize glass fibers and/or nylon tricot and is custom built from a negative plaster mold to suit the individual prior to the attachment of this stump support or leg portion, to the appropriate foot 10.

It is in the form of an elongated socket with a distal cup 18 formed as will hereinafter be described. Fenestrations 19 are provided on each side to facilitate the engagement of the stump with the socket with the malleolus extending through the lower areas 20 of the fenestrations or cutouts.

The fitting and fabrication of the stump support portion 17 and its assembly to the foot 10 will hereinafter be described but reference should first be made to FIG. 15 which shows the cross sectional view of the assembled prosthesis.

The distal socket 18 is inserted within the opening of the foot and bonded thereto with the keel portion 21 formed from a fairly dense urethane or the equivalent material. A strip of belting 22 is embedded within this keel portion as shown and secured by means of a metal screw 23 or the equivalent, into the lower wall of the distal cup 18. If necessary, a metal anchor (not illustrated) may be provided within which the screw may engage.

The belt is apertured as indicated by reference character 24 to allow free flow of the urethane 21 during the casting operation and to facilitate the elimination of any air bubbles, etc.

The density of the urethane 21 together with a strip of belting 22 controls the toe break of the foot depending upon the requirements and the density of the heel area 13 of the foot controls the heel compressibility.

The strip casting technique has been found to be the best method for the Syme amputation negative mold. Because the plaster is laid on without tension, there is little if any distortion of tissues.

The Northwestern ring 25 provides good tissue support during casting and also tends to stabilize dislocated heel pads in a more neutral position for good end bearing. A well contoured distal cup 18 is essential for end bearing and the ring suspension method distributes the load while retaining a more natural distal contour.

Figure 2:
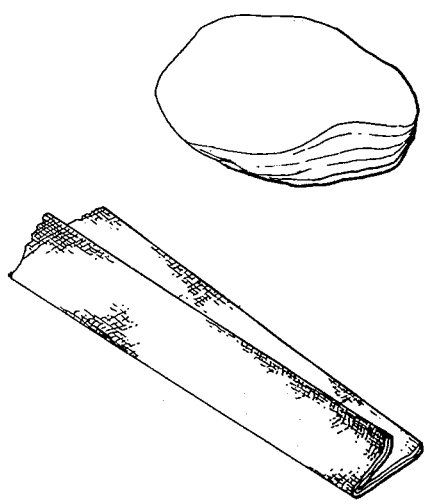
FIGS. 2 to 12 inclusive are schematic views illustrating the fitting and fabrication of the Syme prosthesis.

The average Syme stump requires 3 to 4" rolls of plaster bandage (see FIG. 2) for forming the negative mold. Measure from tibial tubercle to distal stump and cut all three rolls to this length. A piece of 5 ply slab is used for the distal cup 6" long. Clip the corners from the latter.

The strips are folded two at a time to a tapered 4 ply length. They are not folded exactly in half but with a minimum border of ¾" left as 2 ply. This is to allow overlapping of strips without too much bulk. The taper provides greater width at the proximal end where it is needed.

Figure 3:
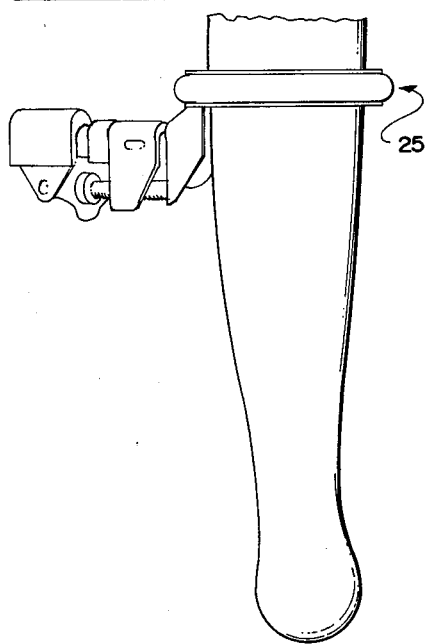
Figure 4:
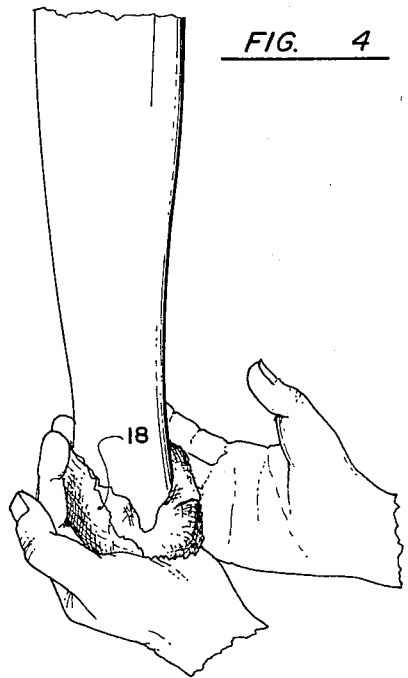
Figure 5:
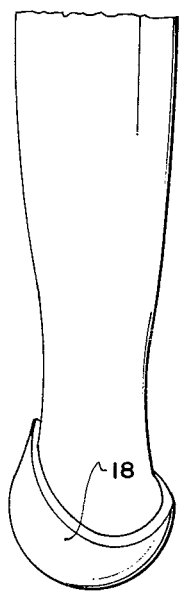

With the amputee suspended in the casting ring 25 (FIG. 3), apply the distal slab first working the plaster well with a cupped palm (FIG. 4). The excess from the coronal plane to anterior is turned down and thickened at the equator of the bulb and pinched to a peak to form a flange. The posterior aspect is left flat as applied (FIG. 5).

Figure 6:
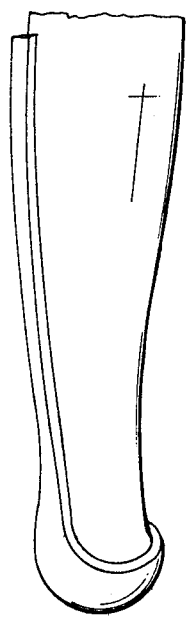
Figure 7:
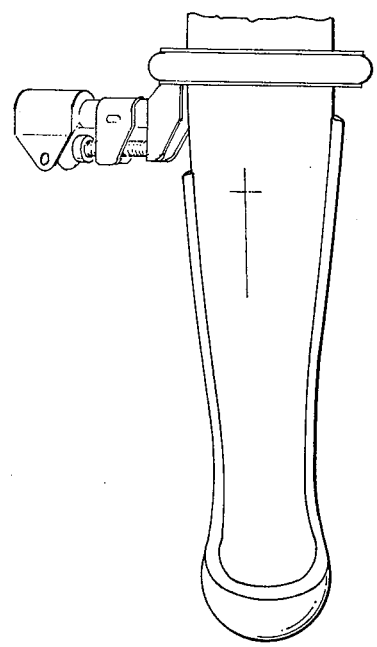

The first strip is laid ⅛" anterior to the coronal plane with the 2 ply edge posterior. After working the plaster in, the leading edge is turned back ¼" and pinched to a peak to blend in with the flange of the distal cup. The most distal portion of the strip is united with the cup to form a single portion of the strip to form a single unit (FIG. 6). Successive strips are laid thin edge upon thick until the opposite coronal plane is reached. The leading edge is thickened as before and blended with the flange of the cup (FIG. 7).

Figure 8:
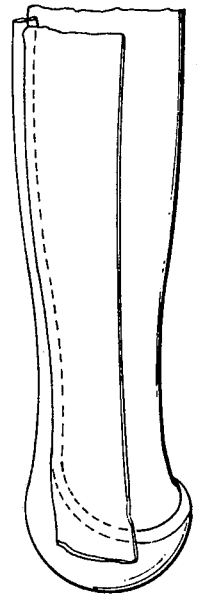
Figure 9:
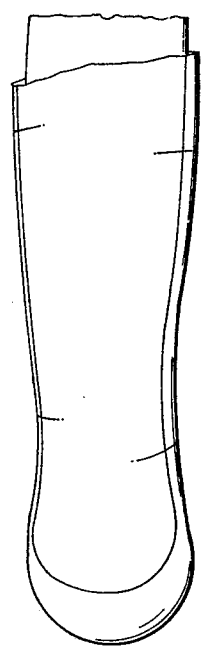

The crest of the tibia is marked on the sock and the entire flange and sock are coated with vaseline. The anterior strips are laid on in the same manner and are thickened against all flanges of the posterior section (FIG. 8). Register lines are struck in several places to assure accurate replacement of the two sections (FIG. 9).

Figure 10:
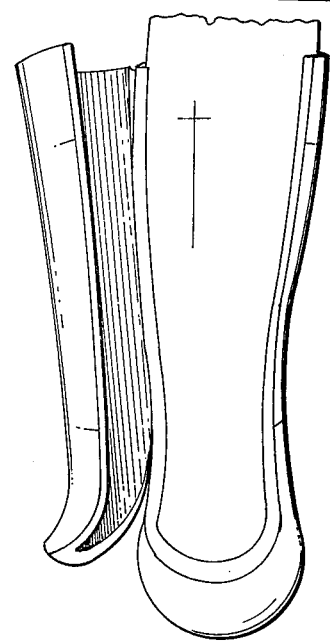
Figure 11:
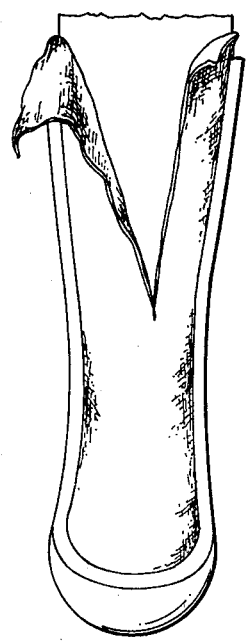

When the plaster has set, the anterior panel is removed and the sock slit for easy removal from the stump (FIGS. 10 and 11), and the stump socket or positive model can now be formed using substantially conventional techniques.

With the strip casting method very little modification is needed. If there are sensitive trigger points, small plaster reliefs can be made. The crest of the tibia should be built up in the area of the pad to a maximum of ⅛" tapering to zero at the outer edge of the pad. It is advantageous to outline the area that the pad will cover. This is a triangle about 4" wide at tibial tubercle tapering down to 1" at the distal end. The length of the pad can be determined by the prominence of the crest. This is usually the proximal two-thirds from tibial tubercle. A light plaster wash and polishing with plastic screen will complete the modifications.

Figure 12:
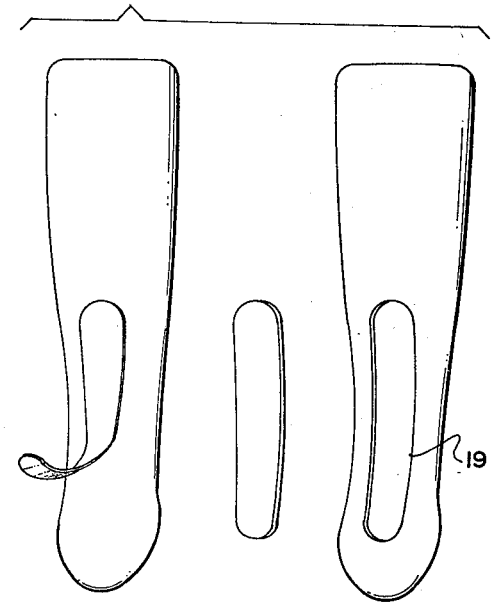

Fenestrations 19 on the stump socket can vary in size depending on the size and configuration of the stump. The average width is 1¼" and the length depends on how bulbous and sensitive the stump is. The longer the openings, the more flexible the anterior and posterior become. A reasonable guide is to measure the greatest circumference of the bulb and mark a point on the calf where the measurement is the same. The patterns are cut from ⅛" kemblo and are radiused on the ends to suit the width. After the model has been lacquered, the patterns are barged on the M & L surfaces. Care should be taken to ensure that the fore and aft columns are of equal widths for the purpose of strength (FIG. 12).

The anterior pad is heated and rolled to approximate shape and barged on the flat side. After the matching surface of the model has been barged and allowed to dry, the pad is appl ied.

If there is a good coating of Hi-Glo or other sealing lacquer on the model, a PVA cap is not required. String is taped to the cast from the kemblo pads to form a vacuum path.

Current recommended lay-up for average construction for the positive model or stump socket 2 perlon
10 glass tricot
2 perlon
(4 perlon proximal only for heady-duty)
Acrylic resin Degaplast 103P or the equivalent.
Lamanierharz 80-20 or the equivalent (40% rigid)
NOTE: Lamanierharz already has 20% flexible resin blended into it so that this must be taken into account.

The stockinette should be cut in double lengths and twisted before it is reflected back to form subsequent layers. The reason for this is to build up the thickness at the distal end to about ¾" which will later be used for fixation of the belting for the keel. The conventional laminating technique is used.

The fenestrations 19 will be clearly outlined through the laminate. These are cut out leaving about ⅛" all around for accurate trimming with a small high speed grinder. Hand sanding is recommended to remove tiny nicks where stresses are apt to cause cracking. A coat or two of lacquer and hand rubbing with a piece of cotton will produce a smooth edge.

The anterior pad is cleaned and installed in the impression it left in the socket. It is best to place it while the barge is wet so it can be "slid" into place.

The proximal brim is trimmed 2" below the tibial tubercle and the edges are smoothed and lacquered.

When fitting the socket or stump support portion 17, for the first time, the amputee should be allowed to don the socket so that he can find the most comfortable method. If he has difficulty passing the distal bulb through the isthmus of the socket, this area can be heated and stretched slightly. Experience has shown that while initial donning is sometimes difficult, the problem will usually dissipate with perseverance.

When comfortable weight bearing has been established, the amputee is ready for alignment. The alignment procedure is carried out with the amputee standing on spacer plates of ¼" thickness. The crests of the ilium are used to establish correct height. The ankles must be a maximum of 4" apart and directly opposite in the coronal plane. A large square is used to mark a vertical line on the lateral aspect of the socket. The posterior aspect is marked in the same manner. This procedure should be carried out three times and the last two checks is done with the square on the first distal mark. If there are any discrepancies at the proximal end, another line is scribed. The final alignment will be a mark midway between the proximal markings. The degree of toe-out is noted in relation to the line of progression. After the length discrepancy has been recorded, the prosthesis is ready for alignment transfer in the vertical transfer jig.

The most secure method of holding the socket in the transfer jig is the plaster and pipe mandrel method. A pipe adaptor is fastened to a mandrel that has been flatened on the distal end. The mandrel is locked into the holding device of the jig and is lowered into the socket to with ⅜" of the inner distal surface. The posterior aspect of the socket faces the column of the jig. A ring of plasticine is used under the socket to stabilize it in the vertical position. Another ring of plasticine is used around the mandrel at the proximal end of the fenestrations 19 to seal off the proximal end of the socket. The vertical lines on the socket are then checked and adjusted. When satisfactory alignment has been achieved, the distal cup 18 and the proximal portion is filled with plaster.

When the plaster has set, the socket is raised and the length discrepancy is established with a surface gauge or the original spacers that were used during the alignment procedure. The length discrepancy can be read directly on the column of the jig for added protection and the locking collar is secured under the holding clamp.

At this time a dry fitting can be done in the Syme foot 10. This is to establish the limits of the foot junction by tracing onto the socket. At the same time, the toe-out is defined on socket and foot with a vertical register marking. Average normal toe-out is usually correct when the anterior tibial crest or the line of progression is aligned with the great toe. The socket 17 may now be removed from the jig and held in a vise in the inverted position. The distal end of the laminate is sanded with coarse sand paper keeping within the outline of the foot tracing. This surface is then treated with MEK (Methyl Ethyl Ketone) or equivalent, and further roughened with a wire brush to raise the surface fibers of the laminate. To further enhance the quality of the foot-socket bond, the area is coated with a 5 minute or rapid setting epoxy or the equivalent, and covered with a piece of nylon stockinette. The outer surface of the nylon is left dry for absorption of the Flexane keel rubber equivalent. The excess stockinette is trimmed about ⅛" proximal to the foot tracing.

A piece of 2"–5 ply belting 22 or similar material and suitable dimensions, is cut to fit the keel cavity 11 of the foot 10. A rotary punch is used to perforate the entire surface (see reference character 24) and punch the hole for fixation to the socket. A #14 ¾" truss head metal screw 23 or similar fastening is used for this purpose and is located centrally on the distal cup 18. Approximate toe-out can be determined when the socket is returned to the vertical jig.

During manufacture a release agent is used on the core of the foot mold resulting in a residual coating on the surface of the cavity 11. This is removed by roughing the inner surface as far as can be reached with the Troutman Router or equivalent. The foot 10 is placed in the shoe (not illustrated) and masked with a sheet of Saran wrap and polyvinyl acetate tape or the like. It is important to use the latter as it will stretch as the socket 17 is lowered into the cavity 11. The socket is raised about 6" above the foot and the entire assembly is ready for final bonding.

The Flexane rubber or equivalent is usually supplied in 1 lb. kits and is adequate for foot sizes up to 28 cm. The mixing instructions supplied with the kit should be followed in every detail to ensure maximum results. When the material has been mixed, the foot cavity is filled slightly to excess and the mating surface of the foot and the socket are coated with the material using a tongue depressor or the like. The socket 17 is now lowered into the cavity 11 until the holding clamp of the jig is resting on the locking collar. Air is expelled along with the excess material by placing a thin screw driver or the like between the junction. Care is taken to eliminate bulge at the toe break by applying pressure at this point. The toe-out markings are aligned at this time and the proximal portion of the foot is taped securely to ensure a close bond of the mating surfaces.

Although the foregoing procedure seems rather messy, final trimming of the excess keel material is remarkably easy after curing. A lino knife or the like is used to remove the unwanted material. A fine bead of coloured lacquer is applied to the junction using a fine water colour brush or a Q-tip applicator. Adequate curing time should be allowed before delivery of the prosthesis.

It will be appreciated that other materials can be used which have equivalent characteristics depending upon availability and design parameters.

Since various modifications can be made in our invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

What we claim as our invention is:

1. A Syme foot prosthesis comprising in combination a precast foot including a keel cavity and a custom formed stump socket engaged within the opening of the foot, said socket including a distal cup portion, an elastomeric material filling said keel cavity and means securing the distal end of said stump socket within said opening and to said elastomeric material filling said heel cavity.

2. The prosthesis according to claim 1 in which said precast foot includes front and rear extensions above the ankle area of said foot and side gores sweeping downwardly on both sides between said front and rear extensions to adjacent the position of the ankle joint of the wearer.

3. The prosthesis according to claim 1 in which said foot includes a rounded heel contour defining a cushioned heel portion, the resiliency of said cushioned heel portion being pre-determined during manufacture by the type of elastomeric material used.

4. The prosthesis according to claim 2 in which said foot includes a rounded heel contour defining a cushioned heel portion, the resiliency of said cushioned heel portion being pre-determined during manufacture by the type of elastomeric material used.

5. The prosthesis according to claim 1 in which said means to secure the distal end of said stump socket within said opening includes an elongated strip of material such as belting and the like embedded within said elastomeric material within said keel cavity and extending from adjacent the heel area to adjacent the toe area thereof, and fastening means operatively securing said strip material adjacent the rear end thereof, to the distal end of the stump socket.

6. The prosthesis according to claim 2 in which said means to secure the distal end of said stump socket within said opening includes an elongated strip of material such as belting and the like embedded within said elastomeric material within said keel cavity and extending from adjacent the heel area to adjacent the toe area thereof, and fastening means operatively securing said strip material adjacent the rear end thereof, to the distal end of the stump socket.

7. The prosthesis according to claim 3 in which said means to secure the distal end of said stump socket within said opening includes an elongated strip of material such as belting and the like embedded within said elastomeric material within said keel cavity and extending from adjacent the heel area to adjacent the toe area thereof, and fastening means operatively securing said strip material adjacent the rear end thereof, to the distal end of the stump socket.

8. The prosthesis according to claim 4 in which said means to secure the distal end of said stump socket within said opening includes an elongated strip of material such as belting and the like embedded within said elastomeric material within said keel cavity and extending from adjacent the heel area to adjacent the toe area thereof, and fastening means operatively securing said strip material adjacent the rear end thereof, to the distal end of the stump socket.

9. The prosthesis according to claims 1, 2 or 3 in which said stump socket is provided with fenestrations upon either side thereof to facilitate the engagement and disengagement of the said prosthesis with the associated stump of the wearer.

10. The prosthesis according to claims 4, 5 or 6 in which said stump socket is provided with fenestrations upon either side thereof to facilitate the engagement and disengagement of the said prosthesis with the associated stump of the wearer.

11. The prosthesis according to claims 7 or 8 in which said stump socket is provided with fenestrations upon either side thereof to facilitate the engagement and disengagement of the said prosthesis with the associated stump of the wearer.

12. The prosthesis according to claims 1, 2 or 3 in which the elastomeric material is selected from the group comprising a solid urethane and any elastomeric material having the same dynamic properties.

13. The prosthesis according to claims 4, 5 or 6 in which the elastomeric material is selected from the group comprising a solid urethane and any elastomeric material having the same dynamic properties.

14. The prosthesis according to claims 7 or 8 in which the elastomeric material is selected from the group comprising a solid urethane and any elastomeric material having the same dynamic properties.

15. A Syme foot prosthesis for use with a stump socket, comprising in combination a slipper type outer shell formed of elastomeric material and defining a keel cavity, said shell including a sole portion, an upper vamp portion, a rounded heel portion, a front extension extending upwardly from said vamp portion and a rear extension extending up from the rear of said heel portion, side gores around the ankle area of the heel portion sweeping downwardly on each side between said front and rear extensions thereby defining a stump socket opening, an elastomeric material filling said keel cavity and means to secure the associated stump socket within the stump socket opening of the slipper.

16. The prosthesis according to claim 15 in which said foot includes a rounded heel contour defining a cushioned heel portion, the resiliency of said cushioned heel portion being predetermined during manufacture, by the type of elastomeric material used.

17. The prosthesis according to claim 15 in which said means to secure the distal end of said associated stump socket within said opening includes an elongated strip of material such as belting and the like, embedded within said elastomeric material within said keel cavity and extending from adjacent the heel area to adjacent the toe area thereof and fastening means operatively securing said strip material adjacent the rear end thereof, to the distal end of the associated stump socket.

18. The prosthesis according to claim 16 in which said means to secure the distal end of said associated stump socket within said opening includes an elongated strip of material such as belting and the like, embedded within said elastomeric material within said keel cavity and extending from adjacent the heel area to adjacent the toe area thereof and fastening means operatively securing said strip material adjacent the rear end thereof, to the distal end of the associated stump socket.

* * * * *